United States Patent [19]

Banes

[11] Patent Number: 5,122,470
[45] Date of Patent: Jun. 16, 1992

[54] FLOATING CELL CULTURE DEVICE AND METHOD

[76] Inventor: Albert J. Banes, 2021 Bivins Rd., Durham, N.C. 27712

[21] Appl. No.: 215,221

[22] Filed: Jul. 5, 1988

[51] Int. Cl.⁵ .................... C12N 5/00; C12M 3/00
[52] U.S. Cl. .................... 435/240.241; 435/240.24; 435/240.243; 435/284; 435/286; 435/311
[58] Field of Search .......... 435/240, .241, 1, 240.241, 435/240.24, 240.23, 284–286, 311, 818, 287, 240.243, 240.2, 240.1; 210/242.1, 242.2; 47/59–65

[56] References Cited

U.S. PATENT DOCUMENTS

| | | | |
|---|---|---|---|
| 4,382,348 | 5/1983 | Kitsu et al. | 47/59 |
| 4,760,028 | 7/1988 | deBruyne et al. | 435/316 |
| 4,789,601 | 12/1988 | Banes | 435/287 |
| 4,822,741 | 4/1989 | Banes | 435/287 |
| 4,839,280 | 6/1989 | Banes | 435/287 |
| 4,917,793 | 4/1990 | Pitt et al. | 435/284 |

OTHER PUBLICATIONS

Hamilton "Semi-Continuous Atropine Production Using Root Cultures of Atropa Belladonna and Floating Polypropylene Membranes" Abstract No. AAD8-8-03483 of Dissertation Abstracts (1987).
ICN Biomedicals, Inc. Product Brochure "Cellagen Membranes" (Aug. 1987).
Reid et al. "New Techniques for Cutting Differentated Cells" in: Jakoby et al.
Methods in Enzymology: Cell Culture, vol. 58 (1985) pp. 263–278.
Vaughan et al. "Growth and Differentiation of Primary Rat Keratinocytes on Synthetic Membranes" In Vitro Cellular & Developmental Biology, vol. 22, No. 3 (Mar. 1986) pp. 141–149.
Leung, D. Y. M. et al., "A New In Vitro System for Studying Cell Response to Mechanical Stimulation," Experimental Cell Research, 109 (1977) 285–298.
Banes, A. J. et al., "A New Vacuum-Operated Stress-Providing Instrument That Applies Static or Variable Duration Cyclic Tension or Compression to Cells In Vitro," J. Cell sci., 1985.
Somjen, D. et al., "Bone Remodelling Induced by Physical Stress in Prostaglandin $E_2$ Mediated," Biochimica et Biophysica Acta, 627 (1980) 91–100.
Brunette, D. M. et al. "Mechanical Stretching Increases the Number of Epithelial Cells Synthesizing DNA in Culture," J. Cell Sci., 69 (1984) 35–45.
Hasagawa et al. "Mechanical Stretching Increases the Number of Cultured Bone Cells Synthesizing DNA and Alters Their Pattern of Protein Synthesis".
Calcif Tissue Int. 37 (1985) 431–436.
Leung, D. Y. M. et al. "Cyclic Stretching Stimulates Synthesis of Matrix Components by Arterial Smooth Muscle Cells in Vitro," Science, 191 (1976) 475–477.

*Primary Examiner*—Robert J. Warden
*Assistant Examiner*—William H. Beisner
*Attorney, Agent, or Firm*—Webb, Burden, Ziesenheim & Webb

[57] ABSTRACT

A floating cell culture device, and methods for using it, which includes elements both for growing cells and for imparting to the device as a whole. The embodiments of the device generally comprise a generally circular flat membrane encircled by a flotation-imparting rim or ring. Biocompatible materials to which cell cultures may adhere may be incorporated in the flat membrane, which materials when present enable cell cultures to grow on the underside of the membrane floating in contact with a body of liquid cell culture medium. The floating cell culture device has utility as a control substrate in the in vitro flexing of cells, and further has utility in the culturing of human keratinocyte layers and migrating cell cultures and associated assays.

28 Claims, 3 Drawing Sheets

FLOATING CELL CULTURE DEVICE AND METHOD

FIELD OF THE INVENTION

The present invention relates to cell culture substrates which float atop liquid cell culture media, and biocompatible surfaces therefor.

BACKGROUND OF THE INVENTION

Conventional culture plates or bottles used for the propagation of cells in vitro are typically manufactured from polystyrene or glass. The routine method for culturing cells includes inoculating the cells into flasks, single culture dishes or multi-well plates, adding a nutrient medium and incubating the cells under controlled conditions. Alternative methods for the in vitro culturing of cells include growing cells in continuously rolling glass or plastic bottles, so that the cells adhere to the wall of a culture vessel beneath continually rotated medium (cells may alternately be grown in fluted roller bottles that have increased inside surface area), or culturing cells on glass or complex polysaccharide beads, tissue segments or in suspension in a suitable culture medium. With all these methods, the culture medium does not exert any deforming stress upon the cells themselves such as would simulate the in vivo stresses applied by tendons, for example, or the cyclic stresses exerted by the heart or lungs on their constituent cells.

One system for the in vitro flexing of cells in culture is documented in Banes, A. J. et al., "A New Vacuum-Operated Stress-Providing Instrument That Applies Static or Variable Duration Cyclic Tension or Compression to Cells In Vitro," *J. Cell Sci.*, 1985. (Related in vitro systems are documented in Somjen, D. et al., "Bone Remodelling Induced by Physical Stress in Prostaglandin $E_2$ Mediated," *Biochimica et Biophysica Acta*, 627 (1980) 91-100; Leung, D. Y. M. et al., "A New In Vitro System for Studying Cell Response to Mechanical Stimulation," *Experimental Cell Research*, 109 (1977) 285-298; Leung, D. Y. M. et al., "Cyclic Stretching Stimulates Synthesis of Matrix Components by Arterial Smooth Muscle Cells In Vitro," *Science*, 191 (1976) 475-477; Hasagawa et al., "Mechanical Stretching Increases the Number of Cultured Bone Cells Synthesizing DNA and Alters Their Pattern of Protein Synthesis," *Calcif Tissue Int*, 37 (1985) 431-436; and Brunette, D. M. et al., "Mechanical Stretching Increases the Number of Epithelial Cells Synthesizing DNA in Culture," *J Cell Sci*, 59 (1984) 35-45.) An improved system for the in vitro flexing of cells is disclosed in U.S. Pat. No. 4,789,601, issued Dec. 6, 1988, to Banes, A. J., U.S. Pat. No. 4,822,741, issued Apr. 18, 1989, to Banes, A. J., and U.S. Pat. No. 4,839,280, issued Jun. 13, 1989, to Banes, A. J.

When cells are flexed in vitro in liquid culture medium, the question arises whether any changes observed (as compared with the same cells grown under static conditions) are caused directly by the flexing of the cell growth substrate or whether such changes are eventuated by secondary currents or turbulence created within the liquid medium as a result of the flexing of the substrate. Obviously, conventional static cell growth cultures cannot provide a "control" in the investigation of this question; neither substrate flexing nor liquid medium movement is present in such systems. Accordingly, a need remains for a cell growth "control" device which can subject its cells to a liquid cell growth media, which media is agitated by the flexing of a separate cell substrate, but can do so without actually flexing the cells it supports.

SUMMARY OF THE INVENTION

In order to meet this need, and to achieve additional improvements in cell culturing described further below, the present invention is a floating cell culture device which includes means both for growing a cell culture and means for imparting buoyancy or flotation of the device as a whole. The invention comprehends both the device and the methods for using it. A typical embodiment of the invention comprises a generally circular flat membrane consisting of (or coated with) a biocompatible polyorganosiloxane composition wherein the membrane is encircled by a frame or rim-like structure (such as a Styrofoam® brand expanded polystyrene ring) which imparts buoyancy to the membrane. Membrane surfaces may be inoculated with cells, and 10 contacted with and/or floated atop liquid cell culture media, as desired. When the membrane is afloat, no mechanical stress is translated to the cell culture except that caused by currents or turbulence which may be present in the liquid culture medium. The present device thus has utility in providing a "control" cell growth surface for use in conjunction with in vitro flexing of cells. Various embodiments of the floating cell culture device have further utility in the culturing of cell layers which require both liquid medium and air exposure, and in the maintenance of two cell culture layers which, although initially separate, may share liquid cell culture medium and/or may be permitted to migrate relative to each other.

DETAILED DESCRIPTION OF THE INVENTION

Generally, the present invention comprehends any cell culture substrate which may be made to float on the surface of a liquid cell culture medium, and the various methods for implementing cell growth therewith. Initial description of the invention is best made with reference to a first embodiment of the invention, as illustrated in FIGS. 1 and 2.

Figure 1:
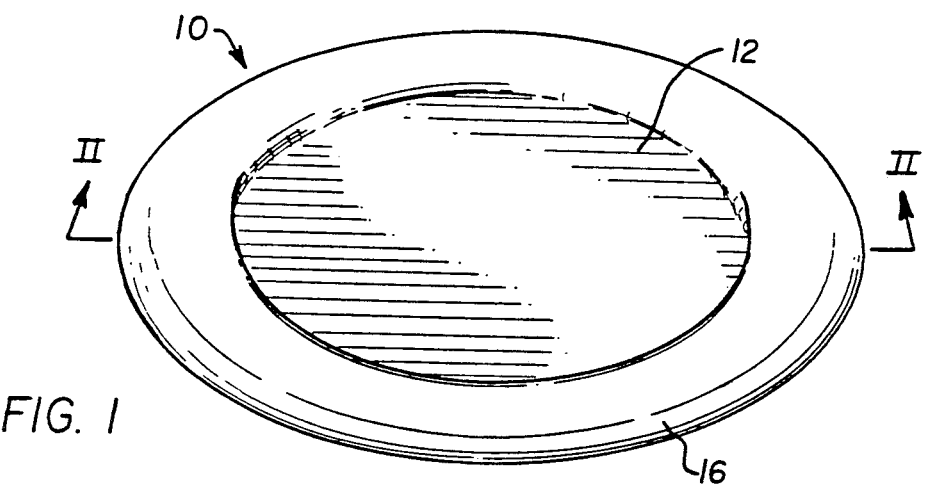
FIG. 1 is a perspective view of a first embodiment of a floating culture device in accordance with the present invention.
Figure 2:
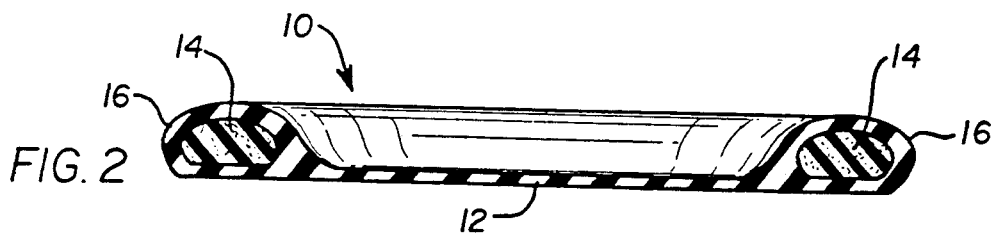
FIG. 2 is a section taken along lines II—II of FIG. 1.

Referring now to FIGS. 1 and 2, the floating cell culture device 10 has a thin, central membrane 12 therein. The underside surface of the central membrane 12 is intended for inoculation with cells to form a cell culture and is adapted to adhere to, to spread and to replicate cells. The central membrane 12 is adapted to float, as described below, so that a nascent cell culture on the underside of the membrane 12 may be placed in contact with a floating upon a body of liquid cell culture medium, i.e., a "floating cell culture."

The central membrane 12 is generally circular in shape and is surrounded at its periphery by a ring-like structure. The ring-like structure is a buoyant ring 14 coated in its entirety with a continuous sheet of the same material which comprises the central membrane 12, which continuous sheet accordingly provides a buoyant ring membrane 16. This structure may be achieved by, for example, passing a buoyant ring 14, fabricated of Styrofoam ® brand expanded polystyrene (or other flotation-imparting material), through a bath of uncured polyorganosiloxane and curing the polyorganosiloxane before the central membrane 12 thus formed can break. Suitable polymers other than polyorganosiloxane include the polyesters, polyurethanes, polyacrylates, polyethers, polyisocyanurates, polycarbonates and polyolefins generally; the polymer selected may be but need not be an elastomer. Those skilled in the art will recognize the viscosity range and other parameters for the uncured polymer within which such a fabrication method may be carried out. An advantage achieved by passing the flotation material entirely through the polymer bath inheres in the moisture-impermeability imparted by the continuous coating produced therewith; even water-sensitive flotation materials, such as open-celled foams and the like, may therefore be incorporated into the buoyant ring 14. Accordingly, flotation materials suitable for use in the first embodiment of the invention include air- or gas-filled natural or synthetic bladders or balloons, open or closed cell foams manufactured of polyisocyanate, polyurethane, polyisocyanurate, polyorganosiloxane, polystyrene, natural or synthetic rubbers or the polyolefins generally, or naturally-occurring flotation materials including textile or vegetable fiber fluffs, batts or mats. In addition, the buoyant ring core 14 may consist of air or lighter-than-the-liquid-medium gases alone or in admixture.

Figure 3:
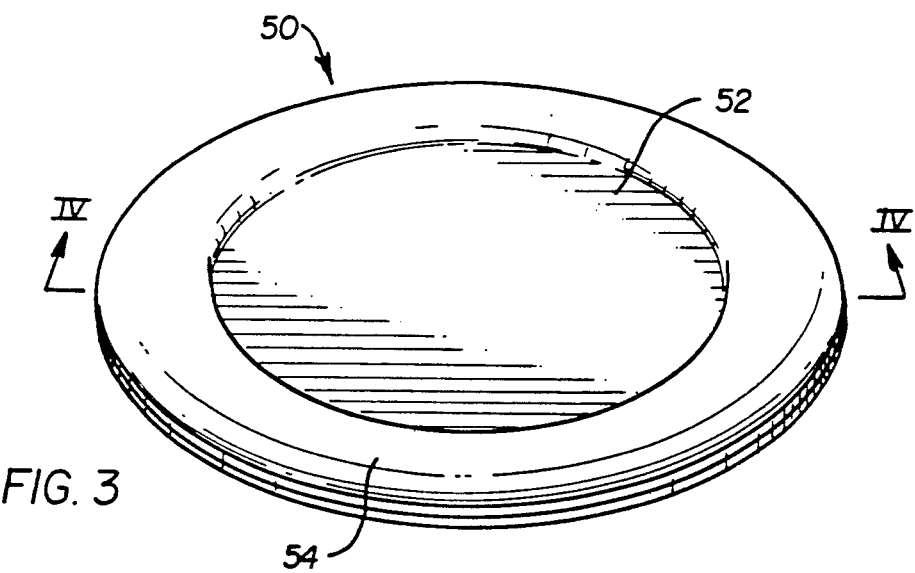
FIG. 3 is a perspective view of a second embodiment of the present floating cell culture device.
Figure 4:
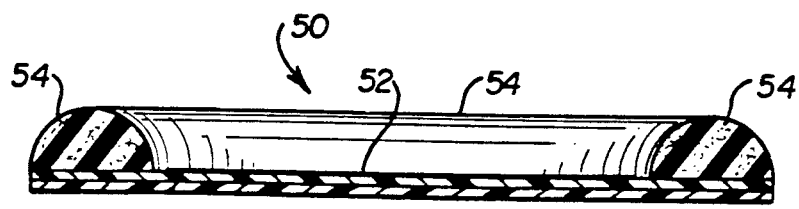
FIG. 4 is a section taken along lines IV—IV of FIG. 3.

Referring now to FIGS. 3 and 4, a second embodiment of the invention is illustrated in which a floating laminated cell culture device 50 has a central membrane laminate 52 central thereto as shown. The central membrane laminate 52 is a biocompatible polyorganosiloxane laminate sheet material. Adhered around the periphery of the generally flat, circular central membrane laminate 52, and to its upper surface, is a buoyant ring 54 fabricated of Styrofoam ® brand expanded polystyrene, to which the central membrane laminate 52 is adhered upon co-curing of the membrane adjacent the expanded polystyrene. The uncured or partially uncured central membrane laminate 52 may be co-cured adjacent the buoyant ring 54 to effect adherence, or the uncured, partially cured or cured central membrane laminate 52 may be co-cured adjacent an uncured material which upon curing yields the buoyant ring 54. Although not a feature of the second embodiment of the invention as illustrated, a central membrane laminate and a buoyant ring optionally may be bonded together by means of a noncytotoxic adhesive composition.

A number of the same flotation materials as listed above are suitable for use in the second embodiment of the invention, with the general exception that such materials must be at least substantially liquid-permeable, or otherwise buoyant in contact with cell culture liquid media, to ensure flotation should the liquid medium wet the buoyant ring 54 during use. Accordingly, the buoyant ring 54 will generally be fabricated of closed-cell foams of polyisocyanate, polyurethane, polyisocyanurate, polyorganosiloxane, polystyrene, natural or synthetic rubbers or the polyolefins, generally. The preferred material for the buoyant ring 54 of the second embodiment is expanded polystyrene.

Preferably, under the circumstances, the central membrane 12 or central membrane laminate 52 in accordance with the present invention is fabricated of a biocompatible polyorganosiloxane composition to which the cells of an in vitro cell culture may readily adhere. Typically, this biocompatible polyorganosiloxane owes its biocompatibility to a surface modification thereto by one of four methods. The composition surface may be embedded with carbon particles, or may be "derivatized" by treatment with a primary amine and optional peptide or by co-curing with a primary amine- or carboxyl-containing silane or siloxane. The derivatization reaction may be carried out on the surface of either an uncured or a cured polyorganosiloxane. In every case, however, derivatization is conducted on the surface of the polyorganosiloxane. It is believed that, when present, the amino or carboxyl groups and optional peptides orient to the surface of the polyorganosiloxane composition and provide the biocompatible surface. According to this theory, chain terminations and/or available hydroxyl groups are oriented to the surface of the polyorganosiloxane, and are available for reaction with the cell culture. One important aspect of the resultant biocompatibility is the ability of cells in culture to adhere even to the underside of a membrane afloat on liquid cell culture medium.

A first method for the derivatization of a cured or uncured polyorganosiloxane membrane comprises embedding the surface with a plurality of elemental carbon particles. For example, an uncured membrane on a release layer may be contacted with a bunsen burner flame both to deposit fine elemental carbon particles on and to cure said surface. The resulting surface demonstrates improved cell adherence over prior art polyorganosiloxane membranes.

The second method for the amination of a cured polyorganosiloxane membrane includes two basic steps. First, the membrane surface is treated for about 30 minutes under ambient conditions, with swirling, with between 0.5 and 1 ml. 1 N. HCl for each $cm^2$ of its surface area. The acid is then decanted. The surface is then contacted, for about 30 minutes and again under ambient conditions, with between 0.5 and 1 ml. 1 M. $NH_4OH$ per $cm^2$ surface. In the alternative, after the acid is decanted the surface may be exposed to ammonia vapor for 15 minutes in a bell jar. The resultant modified surface is washed with water and permitted to dry. Other acids and primary amines may be substituted in stoichiometrically equivalent amounts, such as HFl, HBr (or other halide containing acids) $NH_4Cl$ or $NH_4HCO_3$. It is believed that the surface thus treated demonstrates biocompatibility due to the presence of amino groups pendant from the treated polyorganosiloxane and oriented to the polymer surface. This surface may allow for covalent attachment of proteins by cell-mediated processes; the surface may also allow adsorption of negatively charged compounds which facilitate subsequent cell attachment, adherence and spreading, or further derivatization which may involve a further synthetic step or be cell-mediated.

A third method for treating polyorganosiloxane surfaces includes the amination treatment described above followed by an optional peptidation. After the acidification and amination steps, followed by water washing, the surface is treated by contacting it with between 0.5 and 1 ml. 1 millimolar to 1 nanomolar glutaraldehyde per $cm^2$. Reactive equivalent amounts of other aldehydes be substituted. The glutaraldehyde-treated surface is then contacted with an aqueous peptide which typically has both amine and carboxyl functionalities. The difunctional aldehyde may act not only as a covalent linking moiety but also as a physical spacer arm as well, allowing the subsequently bound peptide species to "rise above" the plane of the polyorganosiloxane base. Ordinarily, the peptide selected will have between 2 and 40 amino acids in linear configuration so as to provide amine and carboxyl functionality at opposing terminal ends of the peptide. However, larger peptides and proteins having molecular weights of several thousand may also be used. A final water wash follows. It is believed that the aldehyde creates a Schiff's base in reaction with the bound amine, leaving a free aldehyde which then reacts with the amino group of the peptide. The resultant aminated/peptidated polyorganosiloxane therefore provides a biocompatible primary amine-containing carboxyl-terminated surface, which biocompatibility is particularly enhanced when the peptide is selected for its adhesion properties for a specific cell culture. For any given application, peptide compatibility may be determined by means known in the art.

A fourth method of amination comprises the co-curing of a polyorganosiloxane with a primary amine- or carboxyl-containing silane or siloxane. (The term "co-curing" signifies that at least one of the adjacent silane- or siloxane-containing compositions is cured in situ.) Exemplary compounds include 3-aminopropyltriethoxysilane, 2-aminoethyltrimethoxysilane, trimethylsilylformic acid, 3-(trichlorosilyl) butanoic acid, and 1,1,1-trichloro-N-(trimethylsilyl) silane-amine. Suitable diluents for the primary amine- or carboxyl-containing silane or siloxane include methoxy trimethylsilane, trimethoxysilane, chlorodimethylsilane and chlorotriisocyanatosilane. The silane or siloxane (with or without silane diluent) is applied in aqueous solution or in aqueous buffer solution at substantially neutral to basic pH to cover the cured or partially cured polyorganosiloxane surface in entirety. Any of the buffers ordinarily used in the preparation of cell culture media are suitable for use as the solvent or carrier for the silane or siloxane such as, for example, the 20 mM HEPES buffer and phosphate buffers well known in the tissue culture arts. Phosphate buffer may be preferable for use with some aminosilyl compounds; HEPES buffer reacts chemically with triethoxysilylpropylamine, for example, whereas phosphate buffer does not. One skilled in the art can easily accommodate these exigencies, or phosphate buffer may simply be used in all applications. The resultant layers are co-cured to room temperature for a period of not less than 15 minutes nor more than twenty-four hours. Curing may be affected at elevated temperatures if desired. The primary amine- or carboxyl-containing silane or siloxane may alternatively be coated onto the uncured polyorganosiloxane, with the subsequent co-curing of the two layers in the same manner as would have been chosen for the curing of the base polyorganosiloxane layer alone. The cured surfaces may be further treated with the optional peptidation or carbon particle embedding treatment described above.

After preparation or fabrication, the composition is washed with water or buffer, sterilized by, for example, ultraviolent light irradiation treatment, and packaged for storage prior to use. Other means of sterilization include microwave energy, gamma radiation and other sterilization means known in the art.

In addition to the above methods, membranes and cell growth substrates may be prepared from known polymers and materials, including the flotation-imparting polymers such as the expanded polystyrene identified above for use as the buoyant ring 14, for particular applications which, for example, do not require cell adherence, optical clarity, etc. These floating cultures are prepared, coated with biocompatible polymer if desired, sterilized and used as are the other floating cell culture devices described herein with one significant difference: if the membrane or cell growth substrate itself is fabricated of a flotation-imparting material, no buoyant ring or other buoyant structure is required (although some graspable, cell-free structure should be provided).

Referring once again to FIG. 4, the central membrane laminate 52 preferably is prepared in accordance with the fourth method described above. As a result, the upper layer of the central membrane laminate 52 comprises a polyorganosiloxane layer and the lower layer comprises a cured amine- or carboxyl-containing silane or siloxane.

The combined structures of the present cell culture device may be fabricated, assembled and joined by means known in the art. Polymer materials may be molded or stamped as desired, and interstructural bonds may be affected by bonding agents or co-curing, i.e., the in situ curing of at least one of the structures to be bonded. As described above, buoyant rings may be passed through one or more baths of uncured polymer, with curing of the polymer before a central membrane thus formed can break. These manufacturing methods, and the molds, mandrels, release layers and other tools they incorporate, are readily apparent to one skilled in the art.

The devices according to the present invention as described above are used as follows. One surface of the biocompatible membrane is inoculated with the cells to be cultured by means known in the art. Ordinarily, the membrane will be inoculated on the underside surface. The device is then placed atop a quantity of liquid culture medium. When the device is used as a "control" substrate in the in vitro flexing of cell cultures, the device is placed atop a quantity of liquid culture medium already in place adjacent a flexing means, such as is described in U.S. Pat. No. 4,789,601, issued Dec. 6, 1988, U.S. Pat. No. 4,822,741, issued Apr. 18, 1989, and U.S. Pat. No. 4,839,280, cited above. The device may be left to support cell growth in static (i.e., non-moving) cell growth medium or, if present in association with a flexing means, the device may be allowed to float in such a way as to prevent exertion of stresses on the supported cells except for those stresses caused by currents or turbulence in the liquid culture medium.

Figure 5:
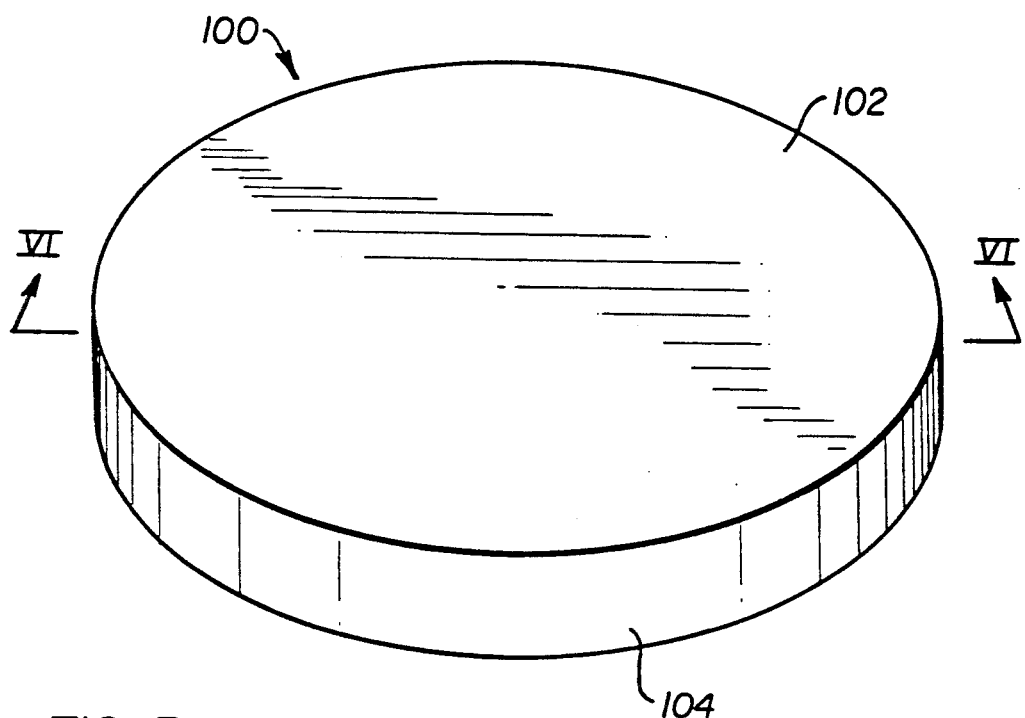
FIG. 5 is a perspective view of a third embodiment of the present floating cell culture device.
Figure 6:
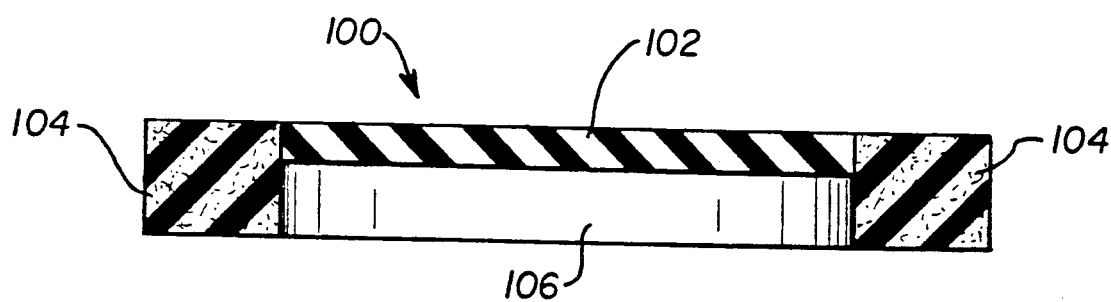
FIG. 6 is a section taken along lines VI—VI of FIG. 5.

FIGS. 5–10 illustrate additional embodiments of the present invention. FIGS. 5 and 6 illustrate a third embodiment of the present floating cell culture device, in which the floating cell culture device 100 comprises a buoyant ring 104 and a thin, central membrane 102. The buoyant ring 104 is fabricated of expanded polystyrene such as Styrofoam ®, but unlike the rounded surfaces of the buoyant ring 14 or 54 shown in FIGS. 2 or 4, the buoyant ring 104 has a flat bottom, top and sides as shown. The central membrane 102 is a layer of biocompatible polyorganosiloxane, selected from those discussed above and cured in situ within the center of the buoyant ring 104. When the third embodiment of the floating cell culture device 100 (in the orientation as shown) is floated atop a body of culture medium, a cylindrical air space 106 is maintained between the culture medium and the central membrane 102. This preserved air space may be beneficially used in the culturing of cells on the underside surface of the central membrane 102. The third embodiment of the present floating cell culture device as shown in FIGS. 5 and 6 may also be used in a position inverted to that shown, thus providing a central thin membrane which may contact the surface of a body of liquid cell culture medium with no retained air space.

Figure 7:
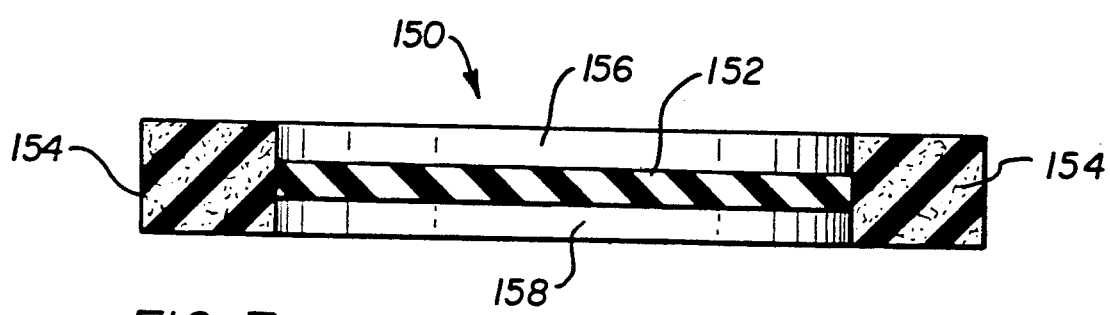
FIG. 7 is a sectional view of a fourth embodiment of the present floating cell culture device.

FIG. 7 illustrates a sectional view of a fourth embodiment of the present floating cell culture device, in which the floating cell culture device 150 comprises a buoyant ring 154 having a thin, central membrane 152. The central membrane 152 is comprised of a biocompatible polyorganosiloxane composition selected from those described above; the central membrane 152 is co-cured in situ with buoyant ring 154. The central thin membrane 152 is affixed to the buoyant ring 154 at the midpoint of the thickness of the buoyant ring and, as a result, the combined structures define an upper and a lower indentation cavity 156, 158. Cells may be grown in either the upper or the lower indentation cavity 156, 158, or both, as necessary. When the floating cell culture device 150 of FIG. 7 is floated atop a body of liquid cell culture medium, in view of the two indentations, an air space between the central thin membrane 152 and the body of liquid cell culture medium is assured. The buoyant ring 154, as shown, is fabricated from Styrofoam ® brand expanded polystyrene.

Figure 8:
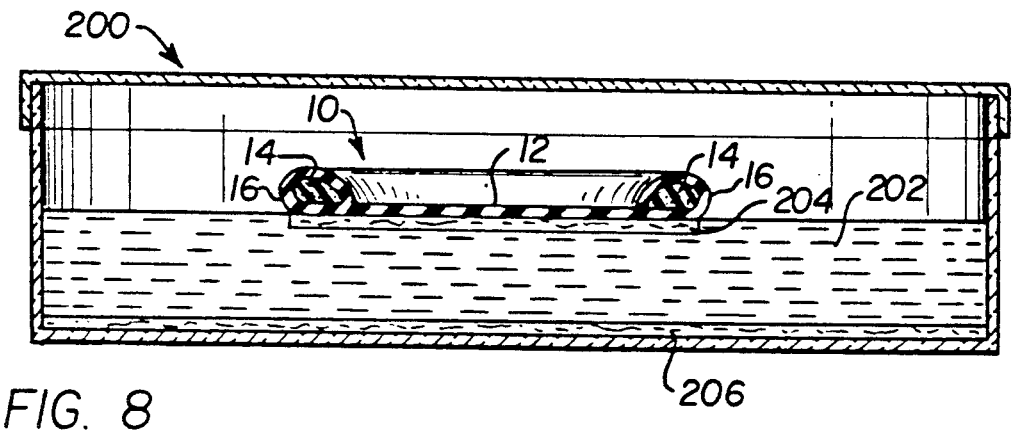
FIG. 8 is a schematic representation, in section, of the floating cell culture device of FIG. 2 afloat on a body of cell culture media contained within a covered laboratory plate.

Referring now to FIG. 8, the floating cell culture device 10 of FIG. 2 is illustrated floating atop a body of liquid cell culture medium 202 in a covered laboratory plate 200. FIG. 8 represents a system which, for example, is particularly suited for the co-culturing of two separate cultures in which the cell cultures are maintained separately but the liquid culture medium which sustains them may traverse freely from one culture to the other.

One application for which the floating cell culture device of FIG. 8 is particularly suited is described as follows. In traditional cell culture apparatus, human keratinocytes (human epidermal cells) have been difficult to grow with any consistent success. It is known that human keratinocytes can be co-cultured with mouse 3T3 cells, with the predominant theory being that the mouse 3T3 cells release an unknown growth factor into the cell culture medium in conjunction with which the human keratinocytes prosper. In view of this discovery, in prior art methods, human keratinocytes have been co-cultured successfully by combining human keratinocytes with mouse 3T3 cells in a single cell culture layer. The resultant cell layer has little or no utility as a human epidermal graft material, however, because the presence of the mouse 3T3 cells in a layer thus produced inevitable results in the immunologic rejection and ultimate failure of any graft tissue so derived.

By means of the system illustrated in FIG. 8, human keratinocyte cells and mouse 3T3 cells may be grown in separate layers in the same liquid culture medium. Referring once again to FIG. 8, a human keratinocyte cell layer 204 adheres to the underside of the biocompatible polyorganosiloxane surface of the central thin membrane 12 of the floating cell culture device 10. A mouse 3T3 cell layer 206 grows in a layer at the bottom of the covered laboratory plate 200, having the liquid cell culture medium 202 therein in conventional fashion. The human keratinocyte cell layer 204 is thus provided with a shared liquid media with respect to the mouse 3T3 cell layer (with concomitant exposure to any unknown "growth factor" actually present therein), yet due to the adherence of the human keratinocyte cell layer 204 to the biocompatible polyorganosiloxane surface of the central membrane 12, the individual cell layers are kept separate. Cross-contamination of either cell culture is ordinarily thus avoided; at worst, keratinocytes will drop onto the mouse cell layer, an event of no practical consequence.

When a human keratinocyte layer is required for transplant or skin grafting, the floating cell culture device 12 may be removed (under sterile conditions) from the covered laboratory plate 200, and may be excised from keratinocyte cell layer thereon, with application of the cell layer directly to a patient wound bed prepared to receive a graft.

Although not shown in FIG. 8, the central membrane 12 of the floating cell culture device 10 may be modified to include a plurality of micropores. Microporous membranes are well known in the cell culture arts, such as the porous nitrocellulose membranes known as Nucleopore ™ membranes, or micropores of various sizes as required may be imparted (by means known in the art) to biocompatible polyorganosiloxane membranes prepared as discussed above. (Porous membranes are discussed further, below.) In the culturing of a human keratinocyte cell layer 204 as shown in FIG. 8, when the supporting central membrane 12 is provided with micropores, the upper surface of the human keratinocyte cell layer 204 is exposed to the air layer present in the covered laboratory plate 200. This air layer exposure simulates the in vivo growth of human epidermal layers in which one side of the cell layer forming the skin is exposed to the air. This in vitro air exposure enhances successful grafting in vivo.

Figure 9:
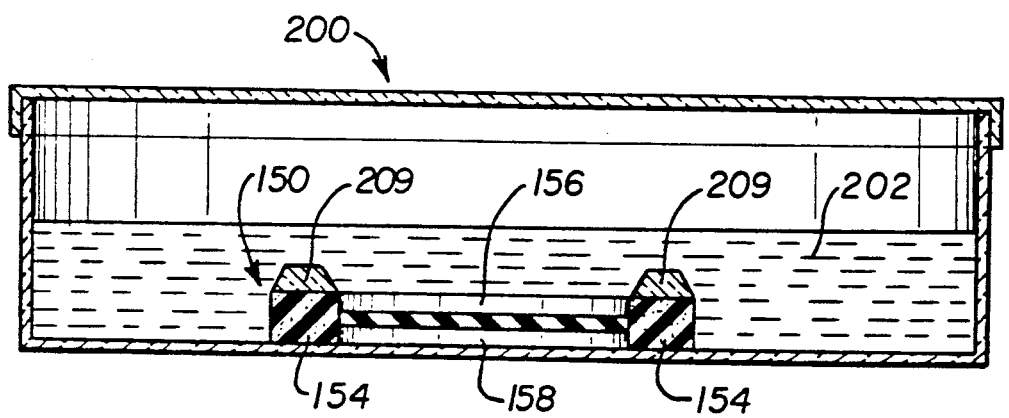
FIG. 9 is a schematic representation, in section, showing the floating cell culture device of FIG. 7 submerged in a body of cell culture media contained within a covered laboratory plate.

Referring now to FIG. 9, the floating cell culture device 150 is submerged within a covered laboratory plate 200 having a layer of liquid cell culture medium 202. The floating cell culture device 150 is kept submerged within the layer of liquid cell culture medium 202 by means of, for example, two glass weights 209. Arrangements such as that shown in FIG. 9, including the weights as shown, have utility when a given cell culture requires initial submersion in liquid cell culture medium with subsequent flotation upon the cell culture medium. Glass is the preferred material for such weights inasmuch as it is a material having known minimal cytotoxicity. Biologically inert stainless steel, titanium or titanium alloy weights may be substituted, as may weights comprised of other materials which do not leach cytotoxic substances into the liquid cell culture medium. The physical configuration of the weights is not central to the present invention and may conform to those known in the art.

Figure 10:
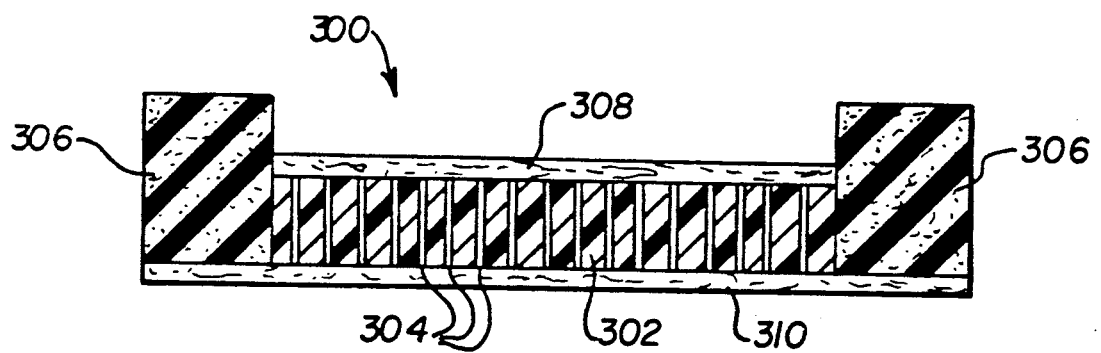
FIG. 10 is a sectional view or a fifth embodiment of the present cell culture device.

Referring now to FIG. 10, a fifth embodiment of a floating cell culture device 300 includes a buoyant ring 306 surrounding and affixed to a central porous membrane 302 having a plurality of pores 304 therethrough. Although the central porous membrane 302 and the pores 304 are shown several times larger than the actual useful embodiments which FIG. 10 represents, the central porous membrane 302 is typically a microporous membrane, such as the porous nitrocellulous membrane available under the trade name Nucleopore ™, generally having pore diameters between about 1 and 100 microns. Thus the fifth embodiment of the invention provides the porous membranes known in the art with the flotation structure of the present invention.

The floating cell culture device 300, as shown in FIG. 10, bears first and second cell populations 308, 310, thereon. The first and second cell populations 308, 310 are in communication by means of the pores 304 in the central porous membrane 302. If the medium and/or the first cell population 308 contains or releases a factor which induces the cells of the second cell population 310 to migrate, such cell migration is made possible by means of the pores 311. The number of cells which migrate can be enumerated and ordinarily are proportional to the concentration of the migration-inducing substance in the opposing cell population and/or growth medium. Although such a floating cell culture device can enable a wide variety of applications, an exemplary use for the device of FIG. 10 is in a biologic assay for the migration-inducing substance. Such an assay bears certain similarities to a chamber migration assay known as the Boyden assay, which does not involve any flotation means.

The invention is further described by means of the following examples.

EXAMPLE I

A polyorganosiloxane composition was prepared by admixing 85 g. Dow-Corning MDX4-4210 clean grade elastomer with 15 g. of the accompanying catalyst and 15 g. of medical grade silicone oil. The components were weighed out in a plastic disposable beaker and were admixed thereafter using the mixing bit of a drill assembly.

Ten Styrofoam ® rings were carved to 0.5 cm thickness maximum, outside diameter 3.0 cm, inside diameter 2 cm. The rings were generally "life saver" shaped, except that the bottom underside of the ring was substantially flat (in the manner of the buoyant ring 14 shown in FIGS. 1 and 2). By means of rubber gloved fingers which had been sprayed with aerosol silicone rubber release agent, the rings were individually dipped into the resin composition in the plastic disposable beaker and were carefully placed atop a release liner for curing. Curing was affected by placing the release paper supporting the rings on a flat metal rack, in an oven set at 60° C., for 45 minutes. (Had curing at elevated temperature been delayed for some reason the rings could have been stored at −20° C. prior to heat processing.) The plates were then removed from the oven and were permitted to equilibrate to room temperature for 30 minutes. A thin, central membrane of polyorganosiloxane resin completely filled the inside diameter of the Styrofoam ® ring. It is estimated that the curing treatment resulted in 90% curing of the polyorganosiloxane resin; although this extent of polymerization is not a required feature of the present invention, it is believed that it may promote later co-curing.

Five milliliters of 98% pure 3-aminopropyltriethoxysilane were admixed in five milliliters of 1 M. phosphate buffer, pH 7.2, with subsequent addition of deionized water to a final volume of 250 ml. Four milliliters of the resultant 3-aminopropyltriethoxysilane solution were then used to coat the underside of each ring to aminate the underside surface. The rings were incubated, inverted on the release liner, at room temperature in the dark for 12 hours. The resultant aminated polyorganosiloxane surfaces at the base of each ring were then rinsed briefly in 2 washes of 20 mM HEPES buffer, followed by a final application of HEPES buffer, which was left in place on the aminated surface for 15 minutes. The rings were sterilized in ultraviolet light in a cell culture hood for 12 hours and were hermetically sealed under sterile conditions in a plastic overwrap.

EXAMPLE II

Floating cell culture devices prepared in accordance with Example I were inoculated with cells on the underside aminated surface of the central thin membrane. The device was placed, underside down, on a quantity of liquid cell culture medium. The ring caused the entire device to float and cell growth was supervised under appropriate incubation.

EXAMPLE III

Floating cell culture devices were prepared in accordance with Example I, except that amination was proceeded by the following method. The underside of each cured central membrane was contacted with 1 ml. 1 N. HCl, followed by decanting and addition of 1 ml. 1 M. $NH_4OH$. Each reagent was left in place for 30 minutes. Washing, drying, sterilization and wrapping were accomplished in accordance with Example I.

EXAMPLE IV

Floating cell culture devices were prepared in accordance with Example III, except that after the $NH_4OH$ addition and water washing, the well bases were treated with glutaraldehyde and peptide as follows.

The underside of each cured central membrane was contacted with 1 ml. 1 nanomolar glutaraldehyde. Each membrane was then contacted with enough of an aqueous peptide having both amine and carboxyl functionality to cover the surface. The peptide selected was 1 mM $NH_2$-RGDS-COOH (R=arginine, G=glycine, D=aspartic acid and S=serine) in water. After one-half hour, the cell culture devices were washed, dried, sterilized and wrapped in accordance with Example I.

EXAMPLE V

The composition in the disposable plastic beaker of Example I was cast, onto a release liner, as a 5.0 ml. thick sheet of polyorganosiloxane. Air bubbles were removed by application of ultrasound to the supporting surface, followed by vacuum and centrifugation. Flat-bottomed 3.0 cm. diameter Styrofoam ® rings were placed, flat side down, at intervals along the sheet. The sheet and adjacent rings were cured over a 45 minute period in an oven set at 60° C.

Upon removal from the oven, the rings were separated with scissors and the polyorganosiloxane resin overhanging each ring was trimmed. The rings were inverted, laminated (and aminated) with 3-aminopropyltriethoxysilane in accordance with Example I, and were washed, dried, sterilized and sealed.

A wide variety of changes and variations may be made in the invention as disclosed without departing from the essence of the invention. The generally circular central membranes disclosed throughout this specification may, of course, be any shape desired. Metal bars or fragments may be implanted in the buoyant ring of the disclosed devices so that the floating cell culture device may be rotationally propelled by an underlying magnetic apparatus typical of laboratory stirring equipment. This rotation would increase the transport of nutrient molecules to the adherent cells and would also stimulate the rate of cell division and other biochemical events in the cells. In addition, substances such as growth promoters may be incorporated in or added to the central membrane or ring, to eventuate an immediate or a time-dependent release of such promoter or other substance to stimulate cell division, migration or some other response. Growth-promoting substance include speciality atmospheres such as nonambient levels of oxygen, carbon dioxide, combinations thereof, etc. Such chemical treatment can come in the final phase of manufacturing of the present floating cell culture device, with the charging of the completed product to a pressurized container containing the promoter, or other substance, to load the promoter or other substance into the polymeric constituents of the device.

Although the invention has been described with reference to special materials and special process, therefore, the invention is to be limited only insofar as is set forth in the accompanying claims. It is to be noted especially that dimensions are not in any way a critical aspect of this invention.

I claim:

1. A floating cell culture device, comprising: a container carrying therein a quantity of liquid cell culture medium having an upper surface thereon, and a membrane suitable for growing a cell culture in suspension within said container, said membrane including means for imparting to said membrane flotation, relative to said liquid cell culture medium, adequate to suspend said membrane adjacent said upper surface of said liquid cell culture medium when said membrane is unrestrained.

2. The floating cell culture device according to claim 1 wherein said means for imparting flotation includes a material selected from the group consisting of air, gas, open-space or closed-cell foams of polyisocyanate, polyurethane, polyisocyanurate, polyorganosiloxane, polystyrene, natural or synthetic rubbers, textile fibers, vegetable fibers, textile fluffs, textile batts and textile mats.

3. The floating cell culture device according to claim 2 wherein said membrane further comprises a cured polymer.

4. The floating cell culture device according to claim 3 wherein said cured polymer is selected from the group consisting polyorganosiloxanes, polyesters, polyurethanes, synthetic rubbers, natural rubbers, polyacrylates, polyethers, polyisocyanurates, polycarbonates, polystyrenes and polyolefin plastics.

5. The floating cell culture device according to claim 4 wherein said polymer further comprises a biocompatible polymer.

6. The floating cell culture device according to claim 5 wherein said biocompatible polymer further comprises a polyorganosiloxane having incorporated at the surface thereof a substance selected from the group consisting of an amine, a carboxylic acid or elemental carbon.

7. The floating cell culture device according to claim 6 wherein said substance is an amine and said amine is a primary amine.

8. The floating cell culture device according to claim 7 wherein said polyorganosiloxane composition further has a peptide incorporated at the surface thereof.

9. The floating cell culture device according to claim 8 wherein said peptide further comprises a carboxyl-terminated peptide.

10. The floating cell culture device according to claim 9 wherein said carboxyl-terminated peptide has amine functionality.

11. The floating cell culture device according to claim 9 wherein said carboxyl-terminated peptide is incorporated at the surface of said polyorganosiloxane by means of its amine functionality.

12. The floating cell culture device according to claim 11 wherein said polyorganosiloxane composition further comprises a cured admixture of clean grade elastomer, medical grade silicone oil and catalyst.

13. The floating cell culture device according to claim 12 wherein said polyorganosiloxane has co-cured at its surface a composition selected from the group consisting of primary amine-containing silanes, carboxyl-containing silanes, primary amine-containing siloxanes and carboxyl-containing siloxanes.

14. The floating cell culture device according to claim 13 wherein said composition co-cured with said polyorganosiloxane is selected from the group consisting of: 3-aminopropyltriethoxysilane, 2-aminoethyltrimethoxysilane, trimethylsilylformic acid, 3-(trichlorosilyl) butanoic acid and 1,1,1-trichloro-N-(trimethylsilyl) silane-amine.

15. The floating cell culture device in accordance with claim 1 wherein said means for imparting flotation is an air-filled bladder.

16. The floating cell culture device according to claim 1 wherein said means for imparting flotation is a ring.

17. The floating cell culture device in accordance with claim 1 wherein said means for imparting flotation is a foam ring.

18. The floating cell culture device according to claim 1 wherein said means for imparting flotation further comprises a closed-cell foam ring.

19. The floating cell culture device in accordance with claim 1 wherein said means for imparting flotation further comprises a closed-cell expanded polystyrene foam ring and said membrane further comprises a polyorganosiloxane membrane.

20. The floating cell culture device according to claim 19 wherein said closed-cell polystyrene ring is co-cured with said polyorganosiloxane membrane.

21. The floating cell culture device according to claim 20 wherein said co-cured closed-cell polystyrene ring and polyorganosiloxane membrane structurally define at least one indentation cavity.

22. The floating cell culture device according to claim 20 wherein said co-cured closed-cell polystyrene ring and polyorganosiloxane membrane structurally define two opposing indentation cavities.

23. The floating cell culture device according to claim 20 wherein said co-cured closed-cell polystyrene ring and polyorganosiloxane membrane structurally define a single indentation cavity.

24. The floating cell culture device according to claim 1 wherein said membrane has pores therein.

25. The floating cell culture device according to claim 24 wherein said membrane having pores therein further comprises a membrane having micropores therein.

26. A method for preparing a floating cell culture wherein cells are inoculated onto the surface of the membrane of the floating cell culture device as set forth in claim 1, followed by the step of floating said membrane containing said cells in said liquid cell culture medium with said cells in contact with said cell culture medium.

27. A method for preparing a cell culture wherein the polyorganosiloxane membrane of the cell culture device according to claim 22, is inoculated with cells in each of said two opposing indentation cavities and said membrane is weighted to a submerged position beneath the surface of said liquid cell culture medium.

28. A method for growing a layer of human keratinocytes, comprising providing a layer of mouse 3T3 cells on a bottom surface of the container of the device as set forth in claim 24, inoculating human keratinocytes onto said membrane of said device, and floating said membrane atop said liquid cell culture medium.

* * * * *